United States Patent
Reddy et al.

(10) Patent No.: US 10,260,106 B2
(45) Date of Patent: Apr. 16, 2019

(54) METHODS AND COMPOSITIONS FOR IDENTIFICATION OF PROSTATE CANCER MARKERS

(71) Applicant: HENRY FORD HEALTH SYSTEM, Detroit, MI (US)

(72) Inventors: G. Prem-Veer Reddy, West Bloomfield, MI (US); Mani Menon, Bloomfield, MI (US)

(73) Assignee: Henry Ford Health System, Detroit, MI (US)

( * ) Notice: Subject to any disclaimer, the term of this patent is extended or adjusted under 35 U.S.C. 154(b) by 181 days.

(21) Appl. No.: 15/217,440

(22) Filed: Jul. 22, 2016

(65) Prior Publication Data

US 2016/0319373 A1    Nov. 3, 2016

Related U.S. Application Data

(63) Continuation-in-part of application No. 12/522,817, filed as application No. PCT/US2008/050775 on Jan. 10, 2008, now abandoned.

(60) Provisional application No. 60/879,634, filed on Jan. 10, 2007.

(51) Int. Cl.
| | | |
|---|---|---|
| *C12Q 1/68* | (2018.01) | |
| *C12Q 1/6886* | (2018.01) | |
| *A61K 31/09* | (2006.01) | |
| *A61K 31/15* | (2006.01) | |

(52) U.S. Cl.
CPC ............ *C12Q 1/6886* (2013.01); *A61K 31/09* (2013.01); *A61K 31/15* (2013.01); *C12Q 2600/158* (2013.01)

(58) Field of Classification Search
CPC .................................................... C12Q 1/6886

USPC ......................................................... 435/6.1
See application file for complete search history.

(56) References Cited

FOREIGN PATENT DOCUMENTS

WO    200246477 A2    6/2002

OTHER PUBLICATIONS

Andersen, Cancer Cell, 17:535-546, 2010.*
Moilanen, Scientific Reports, 2015, 5:12007, pp. 1-11.*
Sgroi, Dennis C., et al. "In Vivo Gene Expression Profile Analysis of Human Breast Cancer Progression", Cancer Research 59, pp. 5656-5661, Nov. 15, 1999.
Falleni, Monica, et al. "Survivin gene expression in early-stage non-small cell lung cancer, Journal of Pathology", 2003; 200, pp. 620-626. Published online May 13, 2003.

* cited by examiner

*Primary Examiner* — Valarie E Bertoglio
(74) *Attorney, Agent, or Firm* — Honigman LLP; Fernando Alberdi; Jonathan P. O'Brien

(57) ABSTRACT

A method for diagnosing and treating prostate cancer in a human subject is provided, the method comprises: a. providing a sample of prostate tissue, blood, or urine from the subject; b. determining the level of expression of SEQ ID NO: 1 and the expression of SEQ ID NO: 5 in the sample, wherein an increased level of expression of SEQ ID NO:1 and a reduced level of expression of SEQ ID NO: 5 in the sample is indicative of a diagnosis that the subject has prostate cancer; and c. administering a therapeutically effective prostate cancer treatment selected from the group consisting of an androgen receptor (AR)-targeted therapy, an antimicrotubule agent, an alkylating agent and an anthracenedione to the subject to treat the prostate cancer in the human subject diagnosed with prostate cancer.

16 Claims, 8 Drawing Sheets

Specification includes a Sequence Listing.

FIGURE 6

| Patient No.: | 19 | | 16 | | 30 | | 2 | | 39 | | 20 | |
|---|---|---|---|---|---|---|---|---|---|---|---|---|
| Tissue: | N | T | N | T | N | T | N | T | N | T | N | T |

TRPM8

Tumor/Non-tumor: 1.69    2.24    1.17    1.74    2.35    2.22

ADAMTS9

Tumor/Non-tumor: 0.71    0.38    0.86    0.76    0.66    0.21

RP11-571N1

Tumor/Non-tumor: 0.82    1.26    1.56    0.68    0.96    1.05

GAPDH

SEQUENCE LISTING

```
<160> NUMBER OF SEQ ID NOS: 16

<210> SEQ ID NO 1
<211> LENGTH: 266
<212> TYPE: RNA
<213> ORGANISM: Homo sapiens

<400> SEQUENCE: 1
cucuaccugc auucccaagu aacggaaagg aguagagguu ugaaucuuau cagauguuau      60
ugucaguccc gcguuggcaa ccucugucug cagaaaugug uaacggucaa uuaauuuguc     120
ucucguuucu gcagcacaca aaauaucaac auagugaacg auguaacagu cugaaaacuu     180
gucucuaacu gguugcagag cuugagcuga caaauaguug aacuauuaag cauucccuga     240
ggcaauacuu uccacugaaa ccuggu                                          266

<210> SEQ ID NO 2
<211> LENGTH: 285
<212> TYPE: DNA
<213> ORGANISM: Homo sapiens

<400> SEQUENCE: 2
accaggtttc agtggaaagt attgcctcag ggaatgctta atagttcaac tatttgtcag      60
ctcaagctct gcaaccagtt agacaagt tttcagactg ttacatcgtt cactatgttg      120
atattttgtg tgctgcagaa acgagagaca aattaattga ccgttacaca tttctgcaga     180
cagaggttgc caacgcggga ctgacaataa catctgataa gattcaaacc tctactcctt     240
tccgttactt gggaatgcag gtagaggaaa ggaaaattaa accac                     285

<210> SEQ ID NO 3
<211> LENGTH: 20
<212> TYPE: DNA
<213> ORGANISM: Artificial Sequence
<220> FEATURE:
<223> OTHER INFORMATION: Forward primer

<400> SEQUENCE: 3
```
tgcctcaggg aatgcttaat                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
cctctacctg cattcccaag                                              20

<210> SEQ ID NO 5
<211> LENGTH: 343
<212> TYPE: DNA
<213> ORGANISM: Homo sapiens

<400> SEQUENCE: 5
ttaccaggtt gaaatgggaa acgagggaga aaggacttga agatgactcc agtgtttcta    60
gtaacacagg tggtgatgtc actaatgagg gtaaaagcac tgaaagcgca ggtatgactt   120
tggaaaatgg tgggtttgag gtgtttcttc ccaagcaagt attggggatt catgccaaga   180
acttaagagt ggtaccaggg ccagacatat aaatttgggg tatttatatc aaatgctggt   240
agaagtagcg agattaaaag agttagccct gagaaaacat agagcaagga gaggcagtta   300
aaatcagcag agcctgctga aaaacacctt ctgtagaagg tag                    343

<210> SEQ ID NO 6
<211> LENGTH: 343
<212> TYPE: DNA
<213> ORGANISM: Homo sapiens

<400> SEQUENCE: 6
ctaccttcta cagaaggtgt ttttcagcag gctctgctga ttttaactgc ctctccttgc    60
tctatgtttt ctcagggcta actcttttaa tctcgctact tctaccagca tttgatataa   120
atacccaaa tttatatgtc tggccctggt accactctta agttcttggc atgaatcccc    180
aatacttgct tgggaagaaa cacctcaaac ccaccatttt ccaaagtcat acctgcgctt   240
tcagtgcttt taccctcatt agtgacatca ccacctgtgt tactagaaac actggagtca   300
tcttcaagtc ctttctccct cgtttcccat ttcaacctgg taa                    343

<210> SEQ ID NO 7
<211> LENGTH: 20
<212> TYPE: DNA
<213> ORGANISM: Artificial Sequence
<220> FEATURE:
<223> OTHER INFORMATION: Forward primer

<400> SEQUENCE: 7 ggtgttttc agcaggctct                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse primer (8)

<400> SEQUENCE: 8
aaaatggtgg gtttgaggtg                                              20

```
<210> SEQ ID NO 9
<211> LENGTH: 21
<212> TYPE: DNA
<213> ORGANISM: Artificial Sequence
<220> FEATURE:
<223> OTHER INFORMATION: Forward primer

<400> SEQUENCE: 9
gattttcacc aatgaccgcc g                                            21

<210> SEQ ID NO 10
<211> LENGTH: 17
<212> TYPE: DNA
<213> ORGANISM: Artificial Sequence
<220> FEATURE:
<223> OTHER INFORMATION: Forward primer

<400> SEQUENCE: 10
ccccagcatt gatgtcg                                                 17

<210> SEQ ID NO 11
<211> LENGTH: 24
<212> TYPE: DNA
<213> ORGANISM: Artificial Sequence
<220> FEATURE:
<223> OTHER INFORMATION: Forward primer

<400> SEQUENCE: 11
caggggaaac agacgatgac aact                                         24

<210> SEQ ID NO 12
<211> LENGTH: 21
<212> TYPE: DNA
<213> ORGANISM: Artificial Sequence
<220> FEATURE:
<223> OTHER INFORMATION: Reverse primer

<400> SEQUENCE: 12
tgcggtaacc caagccacac t                                            21

<210> SEQ ID NO 13
<211> LENGTH: 24
<212> TYPE: DNA
<213> ORGANISM: Artificial Sequence
<220> FEATURE:
<223> OTHER INFORMATION: Forward primer

<400> SEQUENCE: 13
gagccaaaag ttcttctaca ctgc                                         24

<210> SEQ ID NO 14
<211> LENGTH: 22
<212> TYPE: DNA
<213> ORGANISM: Artificial Sequence
<220> FEATURE:
<223> OTHER INFORMATION: Reverse primer

<400> SEQUENCE: 14
agattccaga tggttctgcc ta                                           22

<210> SEQ ID NO 15
<211> LENGTH: 22
<212> TYPE: DNA
<213> ORGANISM: Artificial Sequence
<220> FEATURE:
<223> OTHER INFORMATION: Forward primer
```

-continued

```
<400> SEQUENCE: 15
gagatccctc caaaatcaag tg                                              22

<210> SEQ ID NO 16
<211> LENGTH: 22
<212> TYPE: DNA
<213> ORGANISM: Artificial Sequence
<220> FEATURE:
<223> OTHER INFORMATION: Reverse primer

<400> SEQUENCE: 16
ccttccacga taccaaagtt gt                                              22
```

METHODS AND COMPOSITIONS FOR IDENTIFICATION OF PROSTATE CANCER MARKERS

CROSS-REFERENCE TO RELATED APPLICATIONS

This application is a continuation-in-part of U.S. patent application Ser. No. 12/522,817, filed on Jul. 19, 2010, now abandoned, which is a U.S. § 371(c) national phase application of International PCT Application No. PCT/US2008/050775, filed on Jan. 10, 2008, now published, which claims priority to and the benefit of U.S. Provisional Patent Application No. 60/879,634 filed Jan. 10, 2007, now expired, the disclosures of all of these applications are hereby incorporated by reference in their entireties in this application.

STATEMENT REGARDING FEDERALLY SPONSORED RESEARCH OR DEVELOPMENT

Work underlying the invention was supported in part by NIH Grant No. R01-DK57864 and DOD Grant No. W81XWH-05-1-0071. The government may have certain rights in the invention.

FIELD OF THE INVENTION

The invention relates generally to the field of prostate cancer.

BACKGROUND

Prostate cancer is the most common form of non-skin malignancy and a leading cause of cancer-related death in men in the United States. Prostate cancer generally targets men over age 50, usually with few or no symptoms of its early stages. Treatment options for prostate cancer, especially for hormone refractory prostate cancer, can be very limited.

Early detection can be important for effective treatment and management of prostate cancer. For two decades serum prostate specific antigen ("PSA") has been used as a marker for prostate cancer detection. The advent of PSA as a biomarker has enabled early detection of prostate cancer and hence improved clinical outcome, and prostate cancer can often be found early by testing the amount of PSA in the blood. However, a low PSA level is not a guarantee of disease-free status, and an elevated PSA level is frequently associated with a negative biopsy. Moreover, elevated serum PSA lacks the specificity required to distinguish prostate cancer from other prostatic disorders, such as benign prostatic hyperplasia ("BPH") and prostatitis (1, 2). Furthermore, PSA lacks the sensitivity to detect a large fraction of early stage tumors, since more than 15% of men with a normal serum PSA level have biopsy-proven prostate cancer (3). In addition, histological confirmation of prostate cancer requires multiple biopsies of the prostate using procedures that are too invasive to repeat at regular intervals. Finally, autopsy data from American men indicates that there is about a 49% lifetime risk of developing prostate cancer. However, the risk of having clinically detected prostate cancer in the same population is less than 18% (28), suggesting that the development and progression of prostate cancer is different in different men. Prostate cancer is a heterogeneous disease (29) whose development and progression involve changes in expression of a number of genes that determine oncogenic transformation, survival, and invasiveness of prostate cancer cells. In this context, reliable detection and prediction of outcome of the disease may benefit from identification of changes in expression of genes that influence disease development and progression.

Thus, an unmet need remains for non-invasive methods to detect markers of prostate cancer with specificity and sensitivity in biological samples, including without limitation, tissues and bodily fluids such as urine or blood.

SUMMARY

In some embodiments, without limitation, the invention comprises methods and compositions for the identification and detection of certain molecular markers for prostate cancer with specificity and sensitivity in biological samples, including but not limited to, human prostate tissue, blood, or urine. In accordance with the invention, novel methods and compositions are provided to detect and manage prostate cancer and related indicators.

In accordance with the invention, the inventors have discovered a methodology for identifying certain particular genes expressed in human that are of particular clinical or scientific interest, as one example only, in identifying and monitoring the treatment of prostate cancer. By detection of markers for these genes at differentially elevated or lowered levels in biological samples, including but not limited to, prostate tissue, blood (including any fraction or fractions thereof), serum, or urine, detection of the presence of prostate cancer in vivo is facilitated.

In some embodiments, without limitation, unique methods and compositions allow detection of the presence of specific markers for prostate cancer in order to assess onset of prostate cancer in human subjects, as well as to monitor the response to therapy. In accordance with the invention, the presence of prostate cancer is detected by screening for expression of certain markers for one or more genes that occur at differentially elevated or suppressed levels when prostate cancer is present in the subject.

In accordance with some embodiments, the inventors adapted and applied a reverse-transcriptase polymerase chain reaction ("RT-PCR") differential display method to first identify mRNA transcripts that are differentially expressed in tumor vs. patient-matched non-tumor prostate tissue. In doing so, the inventors discovered certain mRNA transcripts that were expressed differentially in some but not all tumor specimens examined. To identify mRNA transcripts that are differentially expressed in most tumor specimens, the inventors adapted and applied a method of differential display of pooled tissue samples, for purposes herein, described as "Averaged Differential Expression" ("ADE"). This technique was employed to assess differential display of mRNA from patient-matched non-tumor vs. tumor samples. In doing so, the inventors discovered that at least one certain mRNA transcript was over-expressed in pooled tumor RNA, as well as in the majority of individual tumor RNAs that comprised the pool. The mRNA transcript showed 100% identity to a 285 nucleotide sequence (Accession Number EH613345) in KB208E9 (Accession Number AP000345) (herein SEQ ID. NO: 1.) Similarly, based on ADE analysis, it was also discovered that at least one certain mRNA transcript was down-regulated in pooled samples as well as in the majority of individual tumor RNAs tested. The sequence of this second mRNA transcript showed 100% identity to a 343 nucleotide sequence (Accession Number EH613353) in ITU 442e11 (Accession Number AC007707.14) (herein SEQ ID NO: 5). Differential expression of these mRNA transcripts was also detected by RT- PCR in mRNA isolated from urine and blood samples of prostate cancer patients. It was also discovered that specific cDNA probes of frequently differentially expressed mRNA transcripts identified by ADE, e.g., SEQ ID NOS: 2 and 6, can be used for the detection of prostate cancer in urine and blood samples.

In some embodiments, the invention comprises the analysis of gene expression of markers for prostate cancer in order to diagnose such disorders rapidly using non-invasive urine-based tests. In one embodiment, detection of gene expression uses RT-PCR to uniquely detect SEQ ID. NO: 1 and/or SEQ ID NO: 5, or their respective corresponding nucleic acid or protein analogs, as indicators of the presence of prostate cancer in vivo. In accordance with the instant invention, these indicators become positive earlier in the course of disease than markers such as PSA and are more specific.

Without limiting the invention to only those embodiments disclosed, and without disclaiming any embodiment, in some embodiments, the invention comprises methods for assessing the presence of prostate cancer in a human, comprising the steps of (a) providing a sample of prostate tissue, blood, or urine from a human; and (b) determining the level of SEQ ID NO: 1 in the sample, wherein an elevated level of SEQ ID NO: 1 in the sample is indicative of the presence of prostate cancer in the human Other embodiments may comprise methods for assessing the presence of prostate cancer in a human, comprising the steps of: (1) providing a sample of prostate tissue, blood, or urine from a human; and (b) determining the level of SEQ ID NO: 5 in the sample, wherein a reduced level of SEQ ID NO: 5 in the sample is indicative of the presence of prostate cancer in the sample. Still other embodiments may methods for assessing the presence of prostate cancer in a human, comprising the steps of: (a) providing a sample of prostate tissue, blood, or urine from a human; (b) determining the level of SEQ ID NO: I in the sample; (c) determining the level of SEQ ID NO: 5 in the sample; and (d) determining the ratio of the level of SEQ ID NO: 1 in the sample to the level of SEQ ID NO: 5 in the sample, wherein an increase in the ratio is indicative of the presence of prostate cancer in the human.

In further embodiments, the invention comprises novel primers, and kits containing same, for the detection of molecular markers of interest.

BRIEF DESCRIPTION OF THE DRAWINGS

Some embodiments of the invention will now be described, by way of example only, with reference to the accompanying drawings, in which:

FIG. I shows results of mRNA RT-PCR differential display (herein "DD") analysis of RNA from tumor vs. patient-matched non-tumor prostate tissue:

FIG. 6 shows results of RT-PCR analysis of genes identified by DD.

DETAILED DESCRIPTION

Figure 1:
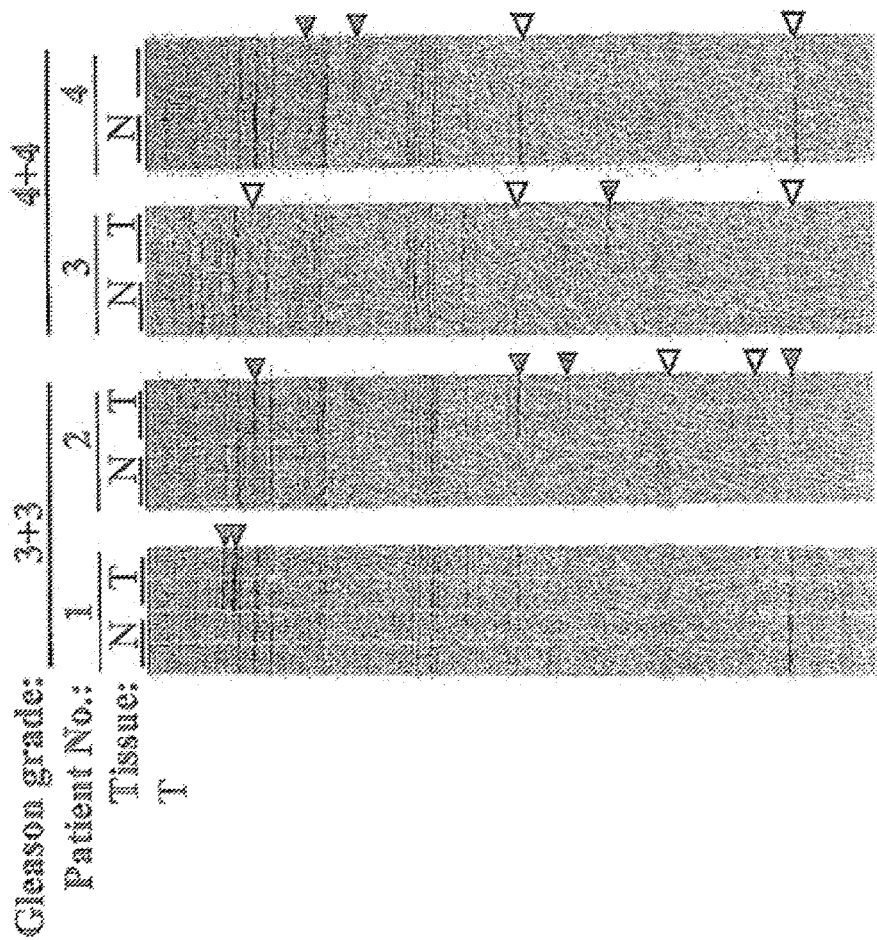

In some embodiments, without limitation, the invention comprises the identification and analysis of one or more markers for gene sequences that are indicative of the presence of prostate cancer in vivo in human subjects.

In accordance with some embodiments, the inventors adapted and applied an RT-PCR differential display method to first identify mR.NA transcripts differentially expressed in tumor vs. patient-matched non-tumor prostate tissue. By doing so, 44 mRNA transcripts were identified that were expressed differentially in some but not all of the tumor specimens examined.

To identify mRNA transcripts that were differentially expressed in most tumor specimens, the inventors adapted and applied a method of differential display of pooled tissue samples, designated "Averaged Differential Expression" ("ADE"). Differential display of mRNA was performed from patient-matched non-tumor vs. tumor tissue, each pooled from ten patients with various Gleason scores. The results showed that differentially expressed mRNA transcripts identified by ADE were fewer in number than by DD. but were expressed in a greater percentage of tumors (>75%) than those identified by differential display of mRNA from individual patient samples. Differential expression of these mRNA transcripts was also detected by RT-PCR in mRNA isolated from urine and blood samples of prostate cancer patients.

Such findings support the inventors' concept that specific cDNA probes of frequently differentially expressed mRNA transcripts identified by ADE can be used for the detection of prostate cancer in biological samples, including without limitation, in urine and blood samples. Thus, Differential Display (DD) (4, 5) was used to investigate and identify mRNA transcripts that are expressed differentially in tumor compared to matched non-tumor prostate tissues from patients who underwent radical prostatectomy. DD analysis is generally known to those of ordinary skill in the relevant art (4, 5, 6, 7). This requires only small amounts of starting RNA and can support rapid identification of over-expressed and down-regulated messages and low abundance mRNAs that are involved in regulatory processes of the cell (8).

In the inventors' work, DD analysis of individual tumors provided information on a number of genes, but the differential expression of several of these genes could be verified by RT-PCR in less than 20% of tumors. The use of DD to compare pooled tumors vs. their pooled non-tumor contra-lateral prostate specimens was further investigated in order to assess whether this method would reveal genes differentially expressed in the majority of samples. This DD of pooled tumors is referred to herein as ADE. Results of testing showed that ADE identified fewer genes than DD of individual tumors; however, their expression was confirmed in >75% of the tumors under study. Furthermore, it was discovered that gene changes identified by ADE were readily detectable in urine and blood of patients with advanced prostate cancer.

Thus, in accordance with some embodiments of the invention, ADE supports the identification of genes whose expression is altered in a wide population of patients with a heterogeneous cancer such prostate cancer. Similarly, the relative levels of over-expressed and down-regulated genes identified in body fluids provide a viable option for reliable and early detection of prostate cancer.

Thus, in accordance with some embodiments of the invention, ADE supports the identification of genes whose expression is altered in a wide population of patients with a heterogeneous cancer such prostate cancer. Similarly, the relative levels of over-expressed and down-regulated genes identified in body fluids provide a viable option for reliable and early detection of prostate cancer, for example, biochemically recurring prostate cancer.

In a related embodiment, the present disclosure provides a method for diagnosing and treating biochemically recurring prostate cancer in a human subject. The early biochemical (PSA) detection of recurrence after definitive local therapy may prompt further treatment. The optimal strategy for such adjunctive therapy, including time of initiation, remains uncertain, and it is the focus of ongoing clinical trials and study. Different definitions of biochemical recurrence exist after surgery and radiation, making it difficult to compare recurrence free survival by time period. To date, it is unknown whether survival is altered by using prostate serum antigen (PSA) values to time the initiation of salvage therapy. Treatment options for recurrence following radical prostatectomy include surveillance, salvage radiation therapy, other forms of focal therapy, androgen deprivation and enrollment in clinical trials evaluating new therapies. Treatment options for recurrence after radiation therapy include surveillance, androgen deprivation, cryotherapy, additional radiation (i.e. brachytherapy), and salvage radical prostatectomy. Salvage therapies in both instances may be more effective if initiated early, but the overall impact of any form of salvage therapy is currently the subject of much study. PSA should reach undetectable levels within 4 weeks after radical prostatectomy. However, a detectable PSA level after this time does not necessarily represent clinically significant recurrent disease. Some patients with detectable PSA levels do not progress because of the presence of benign prostate glands at the margins of resection or from a dormant residual focus of prostate cancer at a local or distant site. Therefore, the ability to identify and diagnose those patients that have certain characteristic biomarkers that directs the patient to aggressive treatment to prevent or treat biochemically recurring prostate cancer is of tremendous value and clinical significance.

To achieve these important treatment measures, the present invention provides a method for diagnosing and treating biochemically recurring prostate cancer in a human subject, the method comprises: a. providing a sample of prostate tissue, blood, or urine from the subject; b. determining the level of expression of SEQ ID NO: 1 and the expression of SEQ ID NO: 5 in the sample, wherein an increased level of expression of SEQ ID NO:1 and a reduced level of expression of SEQ ID NO: 5 in the sample is indicative of the presence of biochemically recurring prostate cancer in the patient's sample; and c. administering a cancer treatment selected from the group consisting of an anti-androgen, an antimicrotubule agent, an alkylating agent and an anthracenedione to the subject to treat the prostate cancer in the human subject if the expression of SEQ ID NO:1 and expression of SEQ ID NO: 5 indicates the presence of biochemically recurring prostate cancer. In some embodiments, the patient having been diagnosed as having biochemically recurring prostate cancer can be treated with an androgen receptor (AR)-targeted therapy. In some illustrative embodiments, an androgen receptor (AR)-targeted therapy can include one or more treatments selected from: drugs that bind to a) the ligand binding domain of AR, for example, enzalutamide, ARN-509, ODM-201; b) drugs that bind to the N-terminal trans activation domain of AR, for example, EPI-001; and c) drugs that inhibit co-regulators of androgen receptor (e.g., calmodulin), for example, hydrazinobenzoylcurcumin (HBC). AR-targeted therapies may also include drugs that suppress dihydrotestosterone (DHT) synthesis, for example, aberaterone, geleterone, and seviteronel. In some embodiments, the cancer treatment described in the exemplary method above includes enzalutamide.

In a further exemplary method, the present disclosure provides a method for diagnosing and treating biochemically recurring prostate cancer in a human subject, the method comprises: a. providing a sample of prostate tissue, blood, or urine from the subject; b. determining the level of expression of SEQ ID NO: 1 and the expression of SEQ ID NO: 5 in the sample, wherein an increased level of expression of SEQ ID NO:1 and a reduced level of expression of SEQ ID NO: 5 in the patient's sample is a diagnosis that the patient has biochemically recurring prostate cancer; and c. administering an androgen receptor (AR)-targeted therapy cancer treatment to the subject to treat the biochemically recurring prostate cancer in the human subject if the subject is diagnosed with biochemically recurring prostate cancer.

In some of these embodiments, the an androgen receptor (AR)-targeted therapy cancer treatment can include administering a therapeutically effective amount of one or more drugs that bind to: a) the ligand binding domain of AR, for example, enzalutamide, ARN-509, ODM-201; b) drugs that bind to the N-terminal transactivation domain of AR, for example, EPI-001; and c) drugs that inhibit co-regulators of androgen receptor, for example, hydrazinobenzoylcurcumin (HBC). AR-targeted therapies may also include drugs that suppress dihydrotestosterone (DHT) synthesis, for example, aberaterone, geleterone, and seviteronel. In some embodiments, the androgen receptor (AR)-targeted therapy cancer treatment described in the exemplary method above includes enzalutamide.

In another exemplary embodiment, the present disclosure provides a method for diagnosing and treating biochemically recurring prostate cancer in a human subject, the method comprises: a. providing a sample of prostate tissue, blood, or urine from the subject; b. determining the level of expression of SEQ ID NO: 1 and the expression of SEQ ID NO: 5 in the sample, wherein an increased level of expression of SEQ ID NO:1 and a reduced level of expression of SEQ ID NO: 5 in the sample is indicative of the presence of biochemically recurring prostate cancer in the patient's sample; and c. administering a therapeutically effective amount and regimen of enzalutamide to the subject to treat the biochemically recurring prostate cancer in the human subject if the subject is diagnosed with biochemically recurring prostate cancer.

In various embodiments, methods for determining the expression of SEQ ID NO: 5 can be achieved in a number of techniques, including, without limitation, polymerase chain reaction (PCR) using an appropriate primer set as exemplified in the examples section herein or by a reverse transcriptase polymerase chain reaction (RT-PCR) assay. As used herein, the determination of the amount of each transcript of SEQ ID NOs: 1 and 5 can be compared to the level of expression of a constitutively expressed housekeeping gene, for example, actin, GADPH and other common housekeeping genes. Once the patient samples (blood, serum, plasma, urine or prostate tissue) has been obtained and levels of expression of SEQ ID NO: 1 and the expression of SEQ ID NO: 5 in the sample have been determined, the assessment of whether the levels of each are up regulated or down regulated can be made by comparing the patient levels of expression of SEQ ID NO: 1 and the expression of SEQ ID NO: 5 to an averaged value for the level of SEQ ID NOs: 1 and/or 5 derived from human prostate tissue samples derived from subjects that do not have prostate cancer. In various embodiments, the control human prostate tissue samples derived from subjects that do not have prostate cancer are age matched, ethnically matched (e.g. Caucasian, African-American, Asian, Latino, etc.) and combinations thereof. In some embodiments, the patient sample is a blood sample. In some embodiments, the whole blood sample has been briefly centrifuged to remove contaminating red blood cells. In other embodiments, the patient sample is a plasma sample. In still further examples, the patient sample is a serum sample. In still further examples, the patient sample is a urine sample. In still further embodiments, the control samples are also the same sample type as the patient's sample being used for comparison, e.g. the patient and control samples are both plasma samples.

In various embodiments, the determination of the level of expression of SEQ ID NO: 1 and the level of expression of SEQ ID NO: 5 in the patient and/or control samples comprises the provision and use of SEQ ID NO: 3 as a forward primer and/or SEQ ID NO: 4 as a reverse primer in the reverse transcriptase polymerase chain reaction assay to determine the level of expression of SEQ ID NO: 1, and the provision and use of SEQ ID NO: 7 as a forward primer and/or SEQ ID NO: 8 as a reverse primer in the reverse transcriptase polymerase chain reaction assay to determine the level of expression of SEQ ID NO: 5.

In some embodiments, after determining the levels of expression of SEQ ID NO: 1 and the level of expression of SEQ ID NO: 5 in the patient and/or control samples, the next step may include, calculating a quotient by determining the level of expression of SEQ ID NO: 1 divided by the level of expression of SEQ ID NO: 5. If the ratio thus determined in the patient is greater than 1.5, then the subject is administered a cancer treatment. For example, if the quotient is greater than 1.5, or greater than 2, or greater than 4, or greater than 5, or greater than 6, or greater than 7, or greater than 8, or greater than 9, or greater than 10, or greater than 15, or greater than 20, the patient is diagnosed as having biochemically recurring prostate cancer. Next the patient is thereby treated with a cancer treatment selected from the group consisting of an anti-androgen, an antimicrotubule agent, an alkylating agent and an anthracenedione to the subject to treat the prostate cancer. In still other embodiments, if the quotient is greater than 4, or greater than 5, or greater than 6, or greater than 7, or greater than 8, or greater than 9, or greater than 10, or greater than 15, or greater than 20, the patient is diagnosed as having biochemically recurring prostate cancer. Next the patient diagnosed as having biochemically recurring prostate cancer is thereby treated with an androgen receptor (AR)-targeted therapy. In some illustrative embodiments, an androgen receptor (AR)-targeted therapy can include one or more treatments selected from: drugs that bind to a) the ligand binding domain of AR, for example, enzalutamide, ARN-509, ODM-201; b) drugs that bind to the N-terminal transactivation domain of AR, for example, EPI-001; and c) drugs that inhibit co-regulators of androgen receptor, for example, hydrazinobenzoyl-curcumin (HBC). AR-targeted therapies may also include drugs that suppress dihydrotestosterone (DHT) synthesis, for example, aberaterone, geleterone, and seviteronel. In some embodiments, the cancer treatment described in the exemplary method above includes enzalutamide.

The following examples of embodiments of the invention are provided without limiting the scope of the invention to only those embodiments disclosed herein and without disclaiming any other embodiments.

EXAMPLES

Materials and Methods—

Tissue specimens: Prostate tumors were obtained from human radical prostatectomy specimens. None of the patients included in the study had received hormonal therapy, chemotherapy, or radiation therapy. The protocol was reviewed and approved by an appropriate Institutional Review Board. Cancerous tissues were graded by a pathologist according to the Gleason scoring system. Non-tumor prostate tissue was obtained from the contra-lateral lobe of the same specimen. Cancer and matched non-tumor tissues were stored frozen at −80° C. within an hour of surgical excision.

Blood and urine specimens: Peripheral blood and urine samples were obtained from prostate cancer patients undergoing chemotherapy. Blood was collected in PAXgene blood RNA tubes for RNA stabilization (Qiagen, Valencia. Calif.). These tubes were stored at RT for at least 2 hours before RNA isolation was performed. Urine was collected in an equal volume of Lysis Buffer containing 5.64 M guanidinium thiocyanate, 0.5% sarcosyl, 50 mM sodium acetate (pH 6.5) and 1 mM f3-mercaptoethanol, and the pH was adjusted to 7.0 with 1.5 M HEPES (pH 8.0); these samples were frozen at −80° C. until extraction of RNA was performed. This procedure allows recovery of total RNA (both intra- and extra-cellular) in urine. All patients provided written informed consent, and protocols were approved by an appropriate Institutional Review Board.

RNA isolation: Total RNA was extracted from frozen prostate tissue specimens with RNeasy Mini Kit (Qiagen, Valencia, Calif.) according to the manufacturer's protocols. For isolation of total cellular RNA from blood, PAXgene Blood RNA Kit was used (Qiagen, Valencia, Calif.). Isolation of RNA from urine was carried out using the protocol of Menke and Warnecke (39). DNA was removed by performing on-column DNase digestion with RNase-free DNase (Qiagen, Valencia, Calif.). The integrity and size distribution of RNA was monitored by agarose gel electrophoresis.

RT-PCR differential display (DD): DD was performed by using the RNAimage Kit (GenHunter, Nashville, Tenn.) as described by Liang and Pardee (5). RNAs isolated from tumor and matched non-tumor prostate tissues obtained from the same surgical specimen were compared by DD. RT-PCR for DD of individual surgical specimens was performed using 24 different primer pair combinations involving 3 anchor primers (H-T11C, H-T11G, and H-T11A) and 8 arbitrary primers (H-AP17 to H-AP24) from GenHunter (Nashville, Tenn.). RT-PCR for DD of pooled surgical specimens from multiple patients (ADE) was performed using anchor primer H-T11C and arbitrary primer H-AP17. Reverse transcription of 200 mg of individual or pooled RNA was performed with Sensiscript RT (Qiagen, Santa Clarita, Calif.). Reactions containing 2 µl 10×RT buffer, 2 µl 5 mM dNTP (final concentration 500 µM), 2 µl 10 µM anchor primer (final concentration 1 µM), 2 µl RT, 1 µl RNase Inhibitor (10 1.411) and 10 IA RNase-free water were incubated at 37° C. for 30 mM and then at 93° C. for 5 mM 10% of the RT reaction was used for subsequent PCR, in duplicate. The PCR reaction contained 200 nM each of anchor primer and arbitrary primer (e.g., H-T11C and H-AP19, or H-T11C and H-AP17), 10 mM Tris-Cl, pH 8.4, 50 mM KCl, 1.5 mM $MgCl_2$. 5 mM DTT, 2 µM dNTP mix, 20 Ci/mmol [a-$^{33}$P]dATP and 2 U Taq Polymerase (Qiagen, Santa Clarita, Calif.) in a total volume of 20 µl. The cycling parameters were 94° C. for 15 sec, 40° C. for 2 min and 72°

C. for 30 sec followed by 72° C. for 5 min. Forty PCR cycles were performed for amplification of RNA from both tumor and patient-matched non-tumor tissues. PCR. products were subjected to denaturing 6% polyacrylamide gel electrophoresis on an extended format using programmable Genomyx LR gel electrophoresis apparatus (Beckman Coulter, Columbia, Md.). cDNA bands that were either more abundant or less abundant in tumor than in non-tumor RNA were excised, re-amplified using the same primers used for DD, and sequenced directly or after cloning into pGEM-T vector (Invitrogen. Carlsbad, Calif.), as described (5). Clones were screened for the insert and then sequenced. Sequences of differentially expressed niRNA transcripts were then searched for homology to known gene sequences in GenBank using the BLAST algorithm (40).

RT-PCR analysis of differentially expressed genes: In order to confirm differential expression of genes identified by DD, semi-quantitative RT-PCR was performed using primers based on the sequence of the DD cDNA fragments. These primer sequences were

```
5'-GATTTTCACCAATGACCGCCG (forward)        (SEQ ID NO: 9)
and

5'-CCCCAGCATTGATGTCG (reverse)            (SEQ ID NO: 10)
for TRPM8.

5'-CAGGGGAAACAGACGATGACAACT (forward)     (SEQ ID NO: 11)
and

5'-TGCGGTAACCCAAGCCACACT (reverse)        (SEQ ID NO: 12)
for ADAMTS9.

5'-GAGCCAAAAGTTCTTCTACACTGC (forward)     (SEQ ID NO: 13)
and

5'-AGATTCCAGATGGTTCTGCCTA (reverse)       (SEQ ID NO: 14)
for RPl 1-571N1.

5'-TGCCTCAGGGAATGCTTAAT (forward)         (SEQ ID NO: 3)
and

5'-CCTCTACCTGCATTCCCAAG (reverse)         (SEQ ID NO: 4)
for KB208E9,

5'-GGTGTTTTTCAGCAGGCTCT (forward)         (SEQ ID NO: 7)
and

5'-AAAATGGTGGGTTTGAGGTG (reverse)         (SEQ ID NO: 8)
for rp11-442e11, and

5'-GAGATCCCTCCAAA.ATCAAC.ITG (forward)    (SEQ ID NO: 15)
and

5'-CCTTCCACGATACCAAAGTTGT (reverse)       (SEQ ID NO: 16)
for GAPDII.
``` cMaster RT$_{plus}$PCR system (Brinkman Instruments Inc, Westbury, N.Y.) was used to reverse transcribe and amplify total RNA from tissue, blood or urine. RNA was reverse-transcribed using oligo (dT) primer and cMaster reverse-transcriptase according to the manufacturer's protocol. The enzyme was inactivated for 5 minutes at 85° C. and cDNA was stored at −80° C. until use Amplification of cDNA was carried out using primers described above for each gene. Different PCR cycle numbers were tested for each gene to ensure that the assay was in the linear range of amplification. The constitutively expressed housekeeping gene GAPDH was amplified from each sample to normalize the level of each test gene. PCR products were run on a 2% agarose gel. Quantitation was carried out by digital analysis of band intensity in the gel with an Eagle Eye II Still Video System, using the EagleSight software (version 3.2; Stratagene, La Jolla, Calif.).

Results

Identification of genes differentially expressed between tumor and non-tumor prostate tissue from radical prostatectomy patients: To attempt to identify biomarkers for prostate cancer detection, DD was performed on tumor and matched non-tumor prostate tissues from prostatectomy patients to investigate differences in expression of numerous genes (5). DD was performed on tissues from 7 patients representing Gleason grades 3+3 (3 patients), 3+4 (1 patient), 4+4 (2 patients) and 5+4 (1 patient), using 24 different anchor and arbitrary primer sets for cDNA amplification. Using this method, the inventors identified 286 differentially expressed cDNA bands (191 over-expressed and 95 down-regulated). Of these 286 bands, 44 (37 over-expressed and 7 down-regulated) have been extracted from the gels and sequenced to date. The Accession Number and gene identity of each of these sequences is presented in Table 1 herein.

TABLE 1

Differentially expressed genes in prostate cancer identified by DD RT-PCR analysis of individual tumors.

| No | Accession Number | Name |
|---|---|---|
| mRNA transcripts over-expressed in prostate cancer |  |  |
| 1 | NM 024080.3 | TRPM8 |
| 2 | NG 001336.2 | T cell receptor gamma locus |
| 3 | BC050454.1 | Dishevelled, dsh homolog 1 |
| 4 | BC016066.1 | Calpastatin mRNA |
| 5 | BC032297.1 | Tripartite motif containing 26, mRNA |
| 6 | NM 001206.1 | BTEB1 |
| 7 | HS353E16 | PITPNB for phosphatidylinositol transfer protein beta |
| 8 | AF483622 | RFC2 |
| 9 | AK023672.1 mRNA | Cisplatin resistance associated over-expressed protein |
| 10 | AC104805.3 | RP11-571N1 |
| 11 | ACO26724.6 | RP11-74N14 |
| 12 | AC1068783 | RP1 I-54K16 |
| 13 | AC106878.3 | RP1I-64809 |
| 14 | AC093619.5 | RP13-741A20 |
| 15 | AC104164.2 | RPII-641C17 |
| 16 | AC055733.16 | RP11-39E3 |
| 17 | AC116098.3 | CTD-2329B17 |
| 18 | AL117329.8 | RP11-191L9 |
| 19 | BC008696.1 | Clone image 2820627 |
| 20 | AC109486.2 | RP1 I-546M4 |
| 21 | AC094086.2 | CTD-2170G1 |
| 22 | AL139194.7 | BAC C-2190GI2 |
| 23 | AC058791.4 | RP1I-138A9 |
| 24 | BC041856.1 | Clone image 5270501 |
| 25 | HS171N11 | RP1-171N11 |
| 26 | AC007032.2 | RP11-22N19 |
| 27 | AC093752.2 | RPII-33B1 |
| 28 | AC1179842 | CTD-2503H21 |
| 29 | AC012598.16 | RP11-237K10 |
| 30 | AY166681.1 | RP4-761 12 on Chr 6 |
| 31 | AC069506.14 | RP11-321G3 |
| 32 | AL513328.12 | RP13-461N9 |
| 33 | AK092048.1 | cDNA FLJ34729 fis, Clone MESAN20064 |

TABLE 1-continued

Differentially expressed genes in prostate cancer
identified by DD RT-PCR analysis of individual tumors.

| No | Accession Number | Name |
|---|---|---|
| 34 | AC090527.3 | RP11-96020 |
| 35 | AC080094.5 | RP11-1007E2 |
| 36 | AL122001.32 | RP4-603114 |
| 37 | AC087525.6 | RP11-321G12 |
|  | mRNA transcripts down-regulated in prostate cancer. | |
| 1 | NM 020249 | ADAMTS9 |
| 2 | BC009175.2 | EBNA1 binding protein mRNA |
| 3 | AL096710 | BPAG1 |
| 4 | AF263545 | HUT11 protein mRNA |
| 5 | HSJ300013 | RP1-300013 |
| 6 | AC108709 | 3BAC RP11-81P15 |
| 7 | AC011295 | BAC RP 11-96,123 |

Of these 44 sequenced mRNAs, only 13 matched mRNA sequences in GenBank; the rest were expressed sequence tags ("ESTs") that had not been reported previously. Thus, in accordance with the inventors' work, by applying DD to tumor and patient-matched non-tumor prostate tissue, a number of new mRNA transcripts were discovered.

FIG. 1 shows results of a representative DD of RNA amplified from tumor vs. patient-matched non-tumor prostate tissue from 4 different patients using the same anchor and arbitrary primer set (H-T11C and 1I-API7). RNA was isolated from prostate tumor ("T" for "tumor") and matched non-tumor ("N" for "non-tumor") prostate tissue from individual patients, and reverse-transcribed with anchor primer H-T11C. The resultant cDNA was amplified with primer H-T11C and arbitrary primer H-AP19 as described in the Materials and Methods. The PCR reactions for each sample were run in duplicate. The amplified products were separated on an extended format 6% polyacrylamide gel. Differentially expressed mRNA transcripts in individual patients are indicated by arrowheads; closed down-regulated mRNA transcripts in tumor, as compared to non-tumor, prostate tissue from individual patients. Tumors of patients 1 and 2 were of Gleason grade 3+3, and those in patients 3 and 4 were of Gleason grade 4+4.

DD performed on different days with the same tissue samples using the same anchor and arbitrary primer pairs yielded essentially the same profile (data not shown). Most of the bands were of similar intensity in matched tumor and non-tumor RNA. However, bands differentially expressed in one tumor/non-tumor pair were not necessarily differentially expressed in other tumor/non-tumor pairs. For example, even tumors with the same Gleason grade differed (compare differentially expressed cDNA bands identified by arrowheads in patients 1 versus 2, both with Gleason grades 3+3, and patients 3 versus 4, both with Gleason grades 4+4).

Of the 44 transcripts listed in Table 1, most were differentially expressed in only one of seven tumors and therefore were not studied further by RT-PCR to evaluate changes in a cross-section of patients. However, a few transcripts were differentially expressed in multiple tumor/non-tumor pairs, and these were analyzed further by RT-PCR with gene specific primers, using RNA isolated from another set of tumor/non-tumor pairs. FIG. 6 shows results of RT-PCR analysis of certain genes identified by DD. TRPM8 (Panel A), ADAMTS9 (Panel B) and RP11-571N1 (Panel C) transcript levels in prostate tumor ("T") and patient-matched non-tumor ("N") prostate tissue were analyzed by RT-PCR using gene-specific primers described in Materials and Methods. GAPDH was included as a housekeeping gene. Band intensities were quantified by densitometry, normalized to GAPDH, and expressed below each panel as a ratio of the transcript level in tumor vs. non-tumor. Patients 19, 16. 30, 2, 39, and 20 had tumors of Gleason grade 3+3, 3+4. 4+3, 4+4, 4+4, and 5+4, respectively.

TRPM8 was found by DD to be over-expressed in 3 of 7 tumors, and RT-PCR confirmed over-expression (>1.5-fold) in another 5 of 6 tumors (FIG. 6). By comparison, in the same tumors, ADAMTS9 was down-regulated (<0.5-fold) in 2 of 6 tumors, and RP I 1571N1 was up-regulated (>1.5-fold) in one of six tumors, frequencies comparable to those found by DD. Thus, DD data correlated with RT-PCR data, and DD showed sensitivity to detect low abundance transcript differences in individual patient samples.

Identification of mRNA transcripts that can detect prostate cancer in a majority of patients using ADE: In order to attempt to increase the odds of identifying transcript differences common to a majority of tumor/non-tumor pairs, DD was carried out using RNA pooled from multiple patients (pooled tumor RNA versus pooled non-tumor RNA). ADE being the term for DD of RNA pooled from multiple patients. As summarized in the results of FIG. 2, RNA was isolated from tumor and patient-matched non-tumor prostate tissues. DD was performed on individual tumor-non-tumor pairs or on pooled tumor vs. pooled non-tumor, using, anchor primer H-T11C and arbitrary primer H-AP17. Two DD profiles of pooled RNA revealed one band higher in tumor in 7 of 10 individual tumor/non-tumor pairs and another band lower in 3 of 5 tumor/non-tumor pairs, respectively. These bands were identified as KB208E9 and rp11-442e11, based on their excision, cloning, sequencing, and BLAST analysis in accordance with methods known to those of ordinary skill. The Gleason grade of the tumors used in our study were 3+3 (patients 15, 17, and 19), 3+4 (patients 18, and 31), 3+5 (patient 23), 4+3 (patients 25 and 30), and 4+4 (patients 2 and 38). [In FIG. 2. "N" =non-tumor tissue; "T" =tumor tissue.]

ADE analysis of RNA pooled from 10 different patient specimens (tumor vs. non-tumor) led to our discovery of an mRNA transcript that was over-expressed in the pooled tumor RNA, as well as in seven of the ten individual tumor RNAs that comprised the pool (FIG. 2A). The sequence of this mRNA transcript showed 100% identity to a 285 nucleotide sequence in KB208E9 (Accession Number AP000345). Based on another ADE analysis of RNA pooled from 5 patient specimens (tumor vs. non-tumor), we also discovered the down-regulation of an mRNA transcript in pooled, as well as in three of the five individual, tumor RNAs (FIG. 2B). The sequence of this mRNA transcript showed 100% identity to a 343 nucleotide sequence in rp1I-442e11 (Accession Number AC007707.14). These two were the only differentially expressed transcripts that were identified by ADE with the one primer pair used.

Sequences of mRNA transcripts identified by the inventors as described herein have been deposited in the GenBank database.

Figure 3:
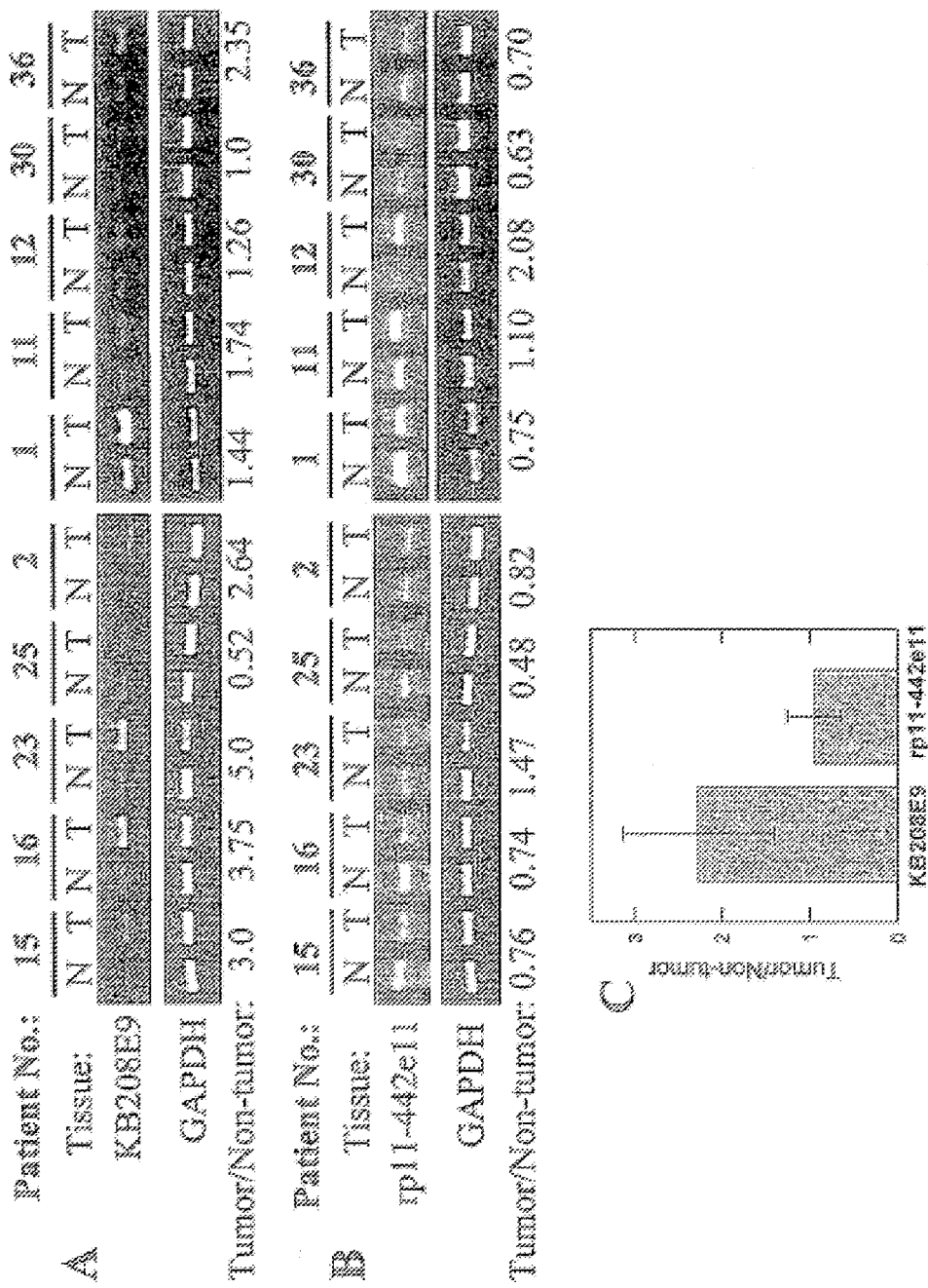
FIG. 3 shows results of RT-PCR analysis of genes identified by ADE in prostate tissue.

RT-PCR validation of differential expression of KB208E9 and rp11-442e11 in prostate tissue from cancer patients: In order to confirm differential expression of genes identified by ADE, RT-PCR with gene-specific primers was used to measure KB208E9 and rp11-442e11 transcript levels in tumor vs. non-tumor pairs from 19 patients. FIG. 3 shows results of RT-PCR using gene-specific primers to analyze the levels of KB208E9 (Panel A) and rp11-442e11 (Panel B) mRNA in tumors and matched non-tumor prostate tissue. GAPDH was included as a housekeeping gene. KB208E9 and GAPDH were amplified using 25 cycles; rp11-442e11, present at lower levels, was amplified using 30 cycles. The number of PCR cycles used for each of these transcripts was determined to be in a linear range for semi-quantitative analysis. KB208E9 (Panel A) and rp11-442e11 (Panel B) were quantitated by densitometry, normalized to GAPDH, and expressed as a ratio in tumor vs. non-tumor (number below each panel). Panel A and B illustrate data from 10 tumor-non-tumor pairs. Panel C summarizes data from these 10 patients plus an additional 9 patients.

Representative RT-PCR results from tissues (tumor vs. non-tumor) of 10 of the 19 patients are presented in FIGS. 3A and 3B. We discovered that KB208E9 was over-expressed in 13 and rp11-442e11 was down-regulated in 12 of these 19 patients. The mean tumor/non-tumor ratio of the KB208E9 transcript, normalized to GAPDH, in 19 patients was 1.96 ±0.263, and the mean tumor/non-tumor ratio of rp11-442e11 was 0.89 ±0.09 (p=0.01) (FIG. 3C). Since both transcripts were analyzed in each tumor vs. non-tumor pairs, the ratio of these transcripts was calculated; the mean ratio of KB208E9/rp11-442e1 1 was 2.13 ±0.27 (n-19). These data indicate that the ratio of KB208E9 to rp11-442c11 can be of diagnostic value.

Detection of KB208E9 and rp11-442e11 in blood and urine of prostate cancer patients: We also investigated whether mRNA transcripts identified by ADE could be detected in body fluids. Blood and urine samples were obtained from nine patients (Table 2 below) undergoing treatment for disseminated prostate cancer.

TABLE 2

Characteristics of prostate cancer patients whose urine and blood specimens were analyzed for KB208E9 and rp11-44e1 1 levels.

| Patient | PSA mg/ml | Gleason Score | Treatment received | Disease status |
|---|---|---|---|---|
| A | 27.4 | 7 | ADT | Rising PSA |
| B | 6.6 | 9 | Chemo | Metastatic |
| C | 1.0 | 8 | Radiation, ADT | Rising PSA |
| D | <0.2 | 6 | ADT | In remission |
| E | <0.2 | 8 | ADT, Radiation | In remission |
| F | 179.4 | Not known | Radiation, Chemo | Metastatic |
| G | 398.6 | 9 | Chemo | Metastatic |
| H | 5.3 | 7 | ADT | Metastatic |
| I | 5.4 | 6 | Radiation | Biochemical relapse |

(ADT. Androgen-deprivation therapy; Chemo, chemotherapy; Radiation, radiation therapy.)

Blood and urine specimens from nine healthy men were used as controls. RNA was prepared from blood and urine and analyzed for KB208E9, rp11-442e11, and GAPDH transcript levels by RT-PCR using gene-specific primers. As represented by the results shown in FIG. 4, RNA was isolated from individual urine specimens, and RT-PCR performed with sequence specific primers for KB208E9, rp11-442e11, and GAPDH. PCR reactions were performed for 30 cycles. Numbers below each panel represent the ratio of KB208E9 to rp11-442e11, based on densitometry. GAPDH is shown as an indicator of RNA in each sample. Panel A shows the level of KB208E9 (probe a) and rp11-442e11 (probe b) in the urine RNA of a healthy man (1-1M1) and 9 prostate cancer patients (A to I). Panel B shows the level of KB208E9 (probe a) and ip11-442e11 (probe b) in urine RNA of nine healthy men (HMI-HM9). Panel C shows the mean ratio of KB208E9 to rp11-442e11 in healthy men (0.66±0.12, n=9) vs. prostate cancer patients (4.04±1.67, n-9). r, Approximate value; a more reliable value could not be obtained because of low rp11-442e11 levels in the sample.]

Figure 4:
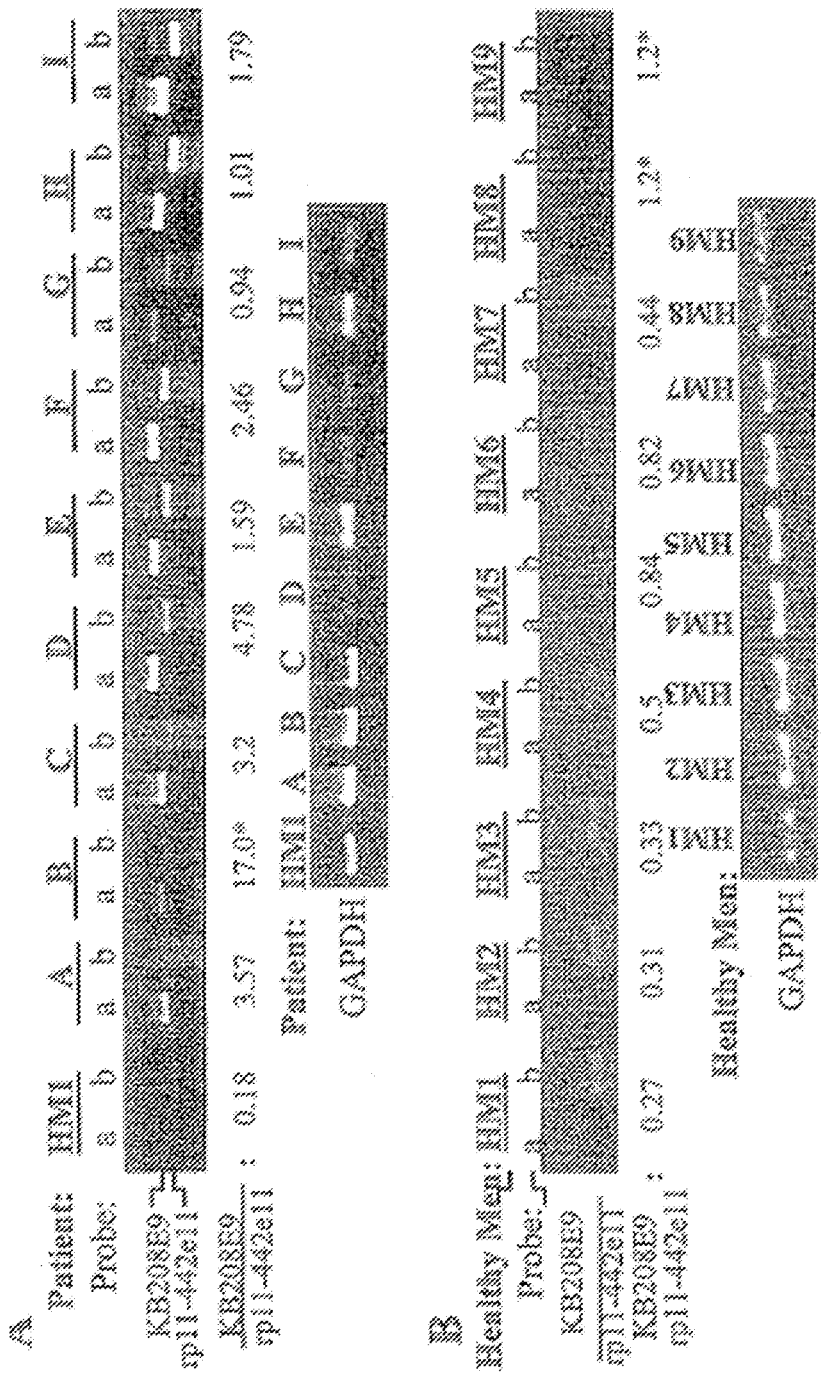
FIG. 4 shows results of RT-PCR analysis of KB208E9 and rp11-442e11 mRNA in urine of prostate cancer patients.
Figure 4:
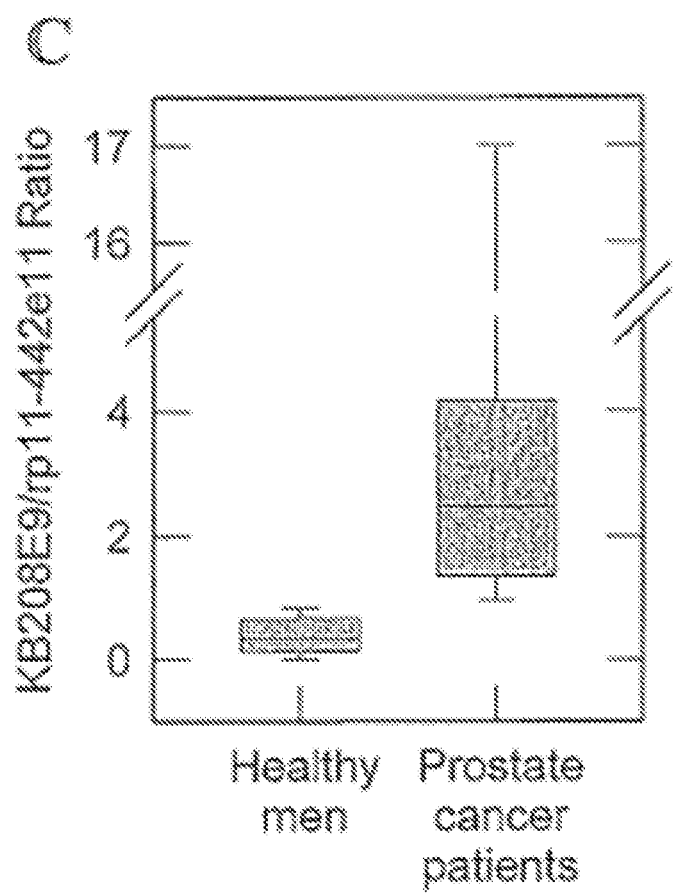

As shown in FIG. 4, KB208E9 (lanes labeled probe a) and rp 11-442e11 (lanes labeled probe b) transcript levels were substantially higher in the urine of patients (FIG. 4A) than of healthy men (FIG. 4B). Most noticeably, the ratio of KB208E9 to rp11-442e11 in urine was 4- to 5-fold higher in prostate cancer patients (4.04±1.67, n=9) than in healthy men (0.66 ±0.12. n=9) (FIG. 4C).

Figure 5:
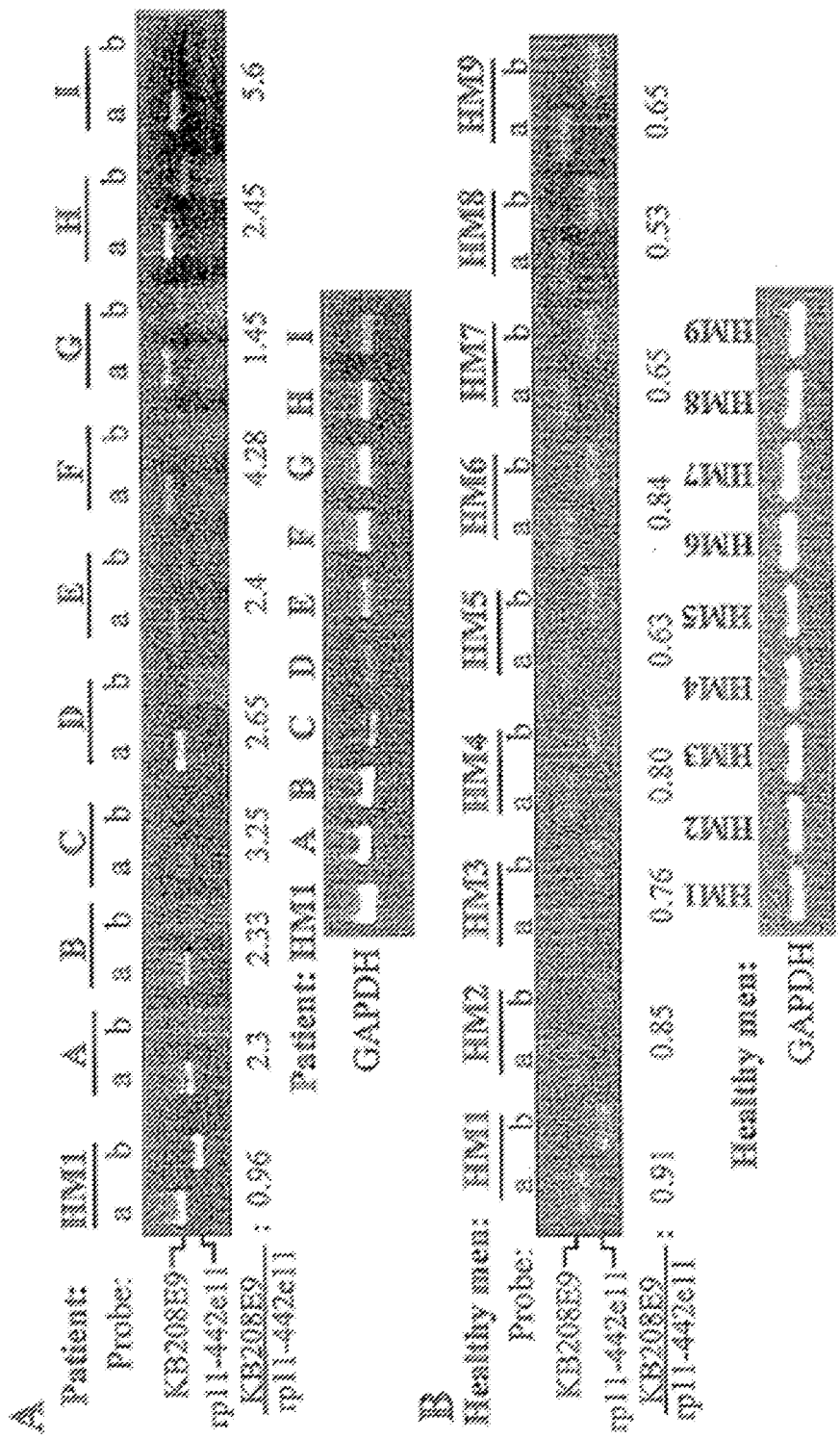
FIG. 5 shows results of RT-PCR analysis of KB208E9 and rp11-4412e11 mRNA in blood of prostate cancer patients.
Figure 5:
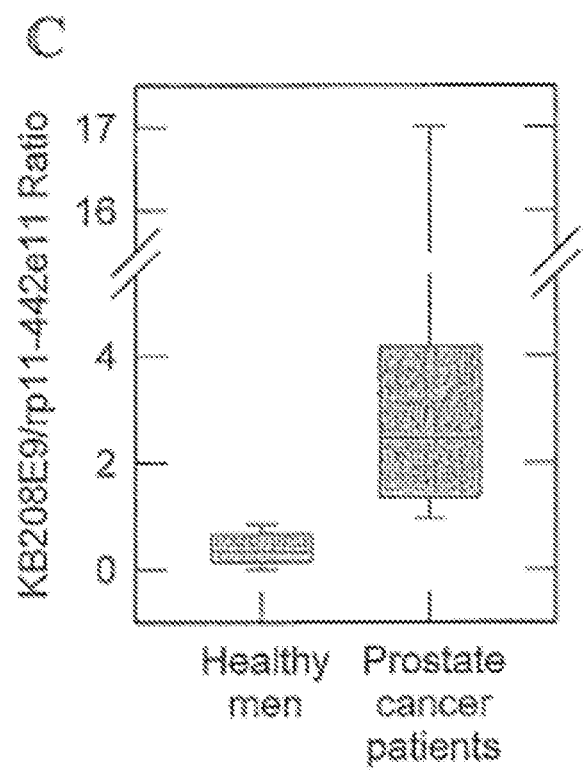

KB208E9 and rp11-442e11 transcripts were also detected in the blood of these subjects (FIG. 5). RNA was isolated from individual blood specimens and RT-PCR was performed with sequence specific primers for KB208E9, rp11-442e11, and GAPDH. PCR reactions were performed for 30 cycles. Numbers below each panel represent the ratio of KB208E9 to rp11-442e11, based on densitometry. GAPDH is shown as an indicator of RNA per sample. Panel A shows the level of KB208E9 (probe a) and rp11-442e11 (probe b) in blood RNA of one healthy man (1-IM1) and 9 prostate cancer patients (A to 1). Panel B shows the level of KB208E9 (probe a) and rp11-442e11 (probe b) in blood RNA of nine healthy men (IM1-HM9). Panel C shows the mean ratio of KB208E9 to rp11-442e11 in healthy men (0.74±0.04, n=9) and prostate cancer patients (2.97±0.42, n=9).

The ratio of KB208E9 to ip11-442e11 was 2.97±0.42 (n=9) in the prostate cancer patients (FIG. 5A) vs. 0.74±0.42 (n=9) in the blood of the healthy men (FIGS. 5B, 5C). Thus, the ratio of KB208E9 to rp11-442e11 in both urine and blood was 4- to 5-fold higher in prostate cancer patients than in healthy men (FIGS. 4C and 5C).

No difference was found in the level of expression of PSA mRNA between tumor vs. non-tumor tissue specimens from prostate cancer patients (data not shown). It is reported that quantitative RT-PCR showed no difference in PSA mRNA levels between blood samples from patients with localized prostate cancer and healthy men (9). Also, no significant difference was observed in PSA mRNA levels between blood samples of patients undergoing treatment for disseminated prostate cancer and healthy men (data not shown). Furthermore, as shown in Table 2, there were also some prostate cancer patients (patients D and E) on androgen-deprivation therapy (ADT) and/or radiation therapy in whom serum PSA levels were below 0.2 ng/ml, yet had detectable levels of KB208E9 in their urine and blood.

Consistent with our work and discoveries, some embodiments of the present invention, without limitation, comprise unique methods and compositions that allow detection of the presence of specific markers indicative of prostate cancer in vivo in order to assess onset of prostate cancer in human subjects, as well as to monitor the response to therapy. Using adapted DD technique, we discovered mRNA transcripts that are expressed differentially in many individual tumors as compared to matched non-tumor prostate tissues from patients who underwent radical prostatectomy. Our identification of 44 differentially expressed mRNA transcripts of which 31 were novel (Table 1). Thus, the majority of the DD mRNA transcripts identified in our study are novel at least in the sense that they do not correspond to transcripts previously deposited in GenBank. The few DD mRNA transcripts that matched GenBank transcripts are reported to be altered in a variety of cancer types.

Particularly noteworthy among the mRNA transcripts that matched sequences in GenBank were TRPM8 and ADAMTS9. TRPM8 was over-expressed and ADAMTS9 was down-regulated in tumors from over 70% of the prostate cancer patients examined (FIG. 6). TRPM8 is a member of the transient receptor potential (TRP) family of Ca$^{++}$-channel proteins that is reported to be androgen-regulated and required for the survival of prostate cancer cells (10), and over-expressed in several cancers including prostate, breast, colorectal and lung (11). ADAMTS9 belongs to a subgroup of the "a distinctive and metalloproteinase with thrombospondin motifs" (ADAMTS) family of enzymes capable of cleaving versican (chondroitin sulphate proteoglycan-2). Increased expression of versican is associated with the local spread of tumor cells, potentially via destabilization of focal adhesion (12). Down-regulation of ADAMTS9 therefore can result in the accumulation of versican in the stromal compartment of the prostate (13). Our observation that ADAMTS9 is down-regulated in prostate tumor tissue is consistent with such a possibility.

The expression profile of most of the genes identified in our work varied from patient to patient (FIG. 1), in part due to the heterogeneous nature of the disease, and in part due to admixture of tumor cells with non-tumor cells. The differential expression of some of these genes could be verified by RT-PCR in less than 20% of tumors. Thus, genes identified by DD of an individual tumor provide information on the expression profile of that individual, but in our work were not themselves determinative of a profile common to all prostate cancer patients.

Our work led to our discovery that a profile common to most prostate cancer patients can he obtained by performing DD on pooled RNAs from multiple patients' tumor and matched non-tumor prostate tissues. Differentially expressed mRNA transcripts identified by ADE were expressed in a greater percentage of tumors (>70%) than those identified by DD of mRNA from individual patient samples, and were fewer in number.

Figure 2:
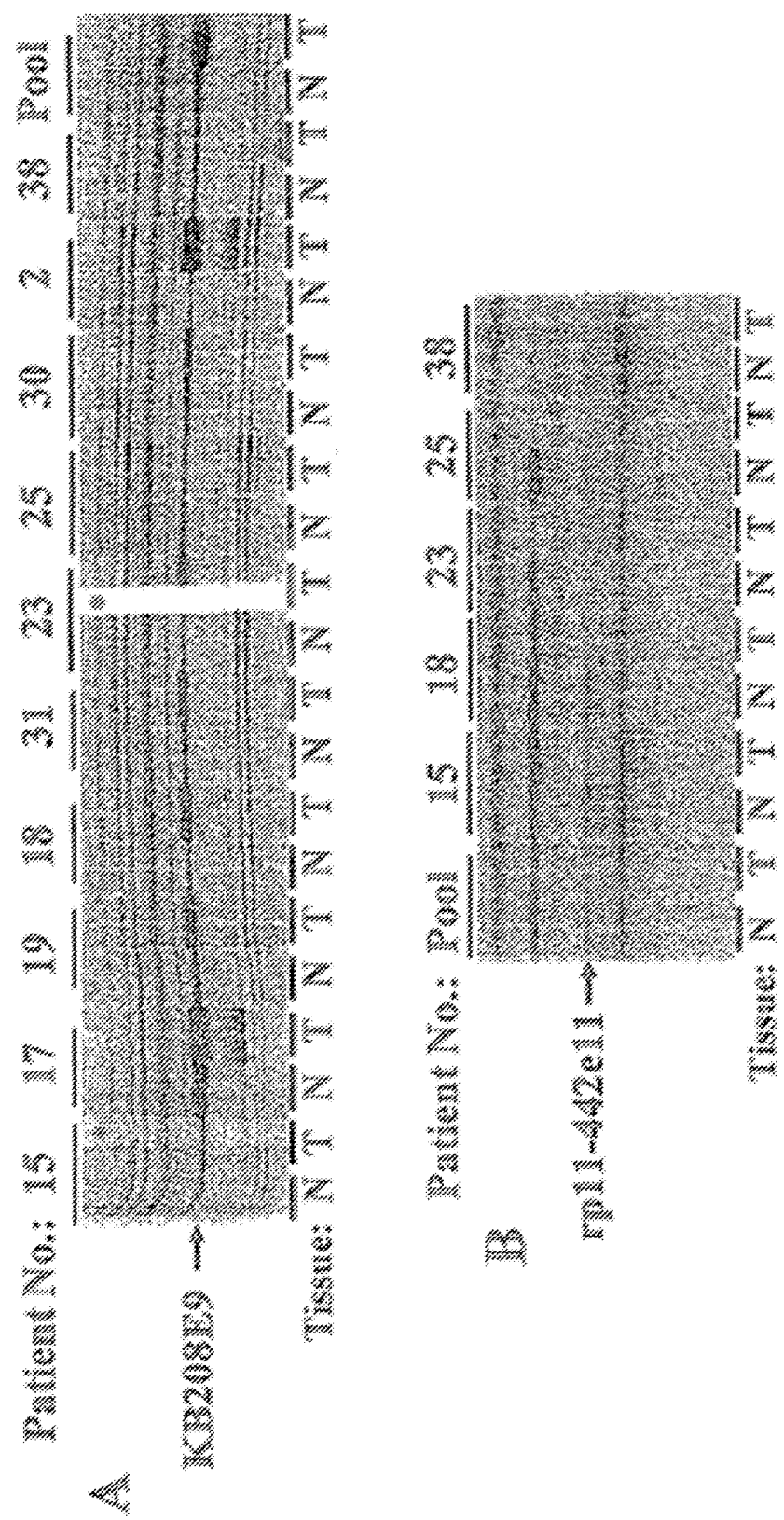
FIG. 2 shows results of averaged differential expression ("ADE") of RNA pooled from multiple patients.

In our work, we discovered with one primer combination that two genes, KB208E9 and rp11-442e11, were differentially expressed in more than 70% of the prostate cancer tumors tested. KB208E9 was elevated in tumor tissues of most patients who underwent radical prostatectomy irrespective of whether they presented with Gleason grade 3, 4, or 5 disease (FIG. 2). A differentially expressed cDNA sequence of 285 nucleotides showed 100% homology to a portion of genomic sequence (clone KB208E9, Accession Number AP000346.1, at Chr22q11.2) that contains no known genes or ESTs. It also had 97% identity with a 277 bp region of human endogenous retrovirus K (HERV-K) mRNA (Accession Number U39937), implicated in certain cancers (I4), and a recent study has shown the presence of HERV-K mRNA in human breast cancer cell lines (15). Another cDNA sequence of 343 nucleotides showed 100% homology to a portion of 2,e110MiC sequence (clone rp11-442e11, Accession Number 007707.14, at chr 11q23.3) that corresponds to intron 4 of the RefSeq gene KIAA0999 (http://genome.ucsc.edu). Thus it appears that prostate cancer expresses decreased levels of an alternate splice variant of K1AA0999 that has not been identified previously.

Thus, in our work, whereas DD in general allowed the detection of novel and low-abundance mRNA transcripts with altered expression in individual patients, ADE identified uncommon mRNA transcripts whose expression is altered in most of the patients.

For two decades early detection of prostate cancer and hence improved clinical outcome can be attributed to the advent of prostate specific antigen (PSA) in serum as a biomarker. However, a low PSA is not a guarantee of disease-free status, and elevated serum PSA lacks the specificity required to distinguish prostate cancer from other prostatic disorders. We observed no difference in the level of expression of PSA mRNA between tumor vs. non-tumor tissue specimens from prostate cancer patients (data not shown).

Circulating epithelial cells in cancer patients permit detection of DNA-(16), protein-(17), and RNA-(18) based prostate cancer markers. It is evident from biochemical recurrence in nearly 25% of patients who have undergone radical prostatectomy for organ-confined prostate cancer (19) that tumor cells can escape from the primary site into the circulation during very early stages of the disease. Prostate epithelial cells indeed have been found in the blood of patients diagnosed with prostate cancer (2, 20-22). It is also evident that at an early stage localized primary tumors may harbor cells with metastatic potential, and exhibit a gene-expression signature matching that observed in metastatic colonies (23, 24). Some genes that are increased in prostate cancer tissue (25, 26) are also found to be elevated in patient urine (27). Thus, cancer cells that enter the circulation even during early stages of tumor growth might display characteristics of cancer that is either likely to metastasize or remain indolent. Therefore we have focused on and accomplished the discovery of certain molecular markers that are sensitive and specific enough to detect prostate cancer in easily obtainable body fluids such as blood and urine.

Thus, in accordance with some embodiments of the inventions, without limitation, certain gene expression changes identified by ADE were readily detectable by .RT-PCR of mRNA isolated from urine and blood of patients undergoing treatment for disseminated prostate cancer; KB208E9 and rp11-442e1 were present at different levels in urine and blood of prostate cancer patients relative to healthy men, and the ratio of KB208E9 to rp11-442e11 was 3- to 4-fold higher in prostate cancer patients (FIGS. 4 and 5); an increase in KB208E9 levels was observed in all patients irrespective of whether the disease was in remission (patients undergoing ADT and/or radiation therapy for biochemical recurrence after radical prostatectomy) or hormone-refractory (metastatic patients undergoing chemotherapy); and the KB208E9/rp11-442e11 ratios of prostate cancer patients compared to healthy men show little or no overlap (FIGS. 4 and 5). Thus, we have discovered that increased KB208E9, reduced rp11-442e11, and/or increased ratio of KB208E9/rp11-442e11 can characterize patients with localized and advanced disease. Our discoveries support the concept that frequently differentially expressed mRNA transcripts identified using ADE can be used for the detection of prostate cancer in body fluids such as urine and blood.

Preferred embodiments of the present invention have been disclosed. A person of ordinary skill in the art would realize, however, that certain modifications would come within the teachings of this invention, and the following claims should be studied to determine the true scope and content of the invention. In addition, the methods and compositions of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive. While the present invention has been particularly shown and described with reference to the preferred and alternative embodiments described herein, it should be understood by those skilled in the art that various alternatives to the embodiments of the invention described herein may be employed in practicing the invention without departing from the spirit and scope of the invention as defined in certain nonlimiting embodiments herein. It is intended that the claims filed herewith define the scope of the invention and that the methods and composition within the scope of these claims and their equivalents be covered thereby. This description of the invention should be understood to include all novel and non-obvious combinations of elements described herein, and claims may be presented in this or a later application to any novel and non-obvious combination of these elements. The described embodiments are illustrative only and do not limit the invention to only those expressly described and do not constitute a disclaimer of other embodiments. No single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

```
                         SEQUENCE LISTING

SEQ ID NO: 1:
KB208E9 mRNA -
CUCUACCUGC AUUCCCAAGU AACGGAAAGG AGUAGAGGUU UGAAUCUUAU

CAGAUGUUAU UGUCAGUCCC GCGUUGGCAA CCUCUGUCUG CAGAAAUGUG

UAACGGUCAA UUAAUUUGUC UCUCGUUUCU GCAGCACACA AAAUAUCAAC

AUAGUGAACG AUGUAACAGU CUGAAAACUU GUCUCUAACU GGUUGCAGAG

CUUGAGCUGA CAAAUAGUUG AACUAUUAAG CAUUCCCUGA GGCAAUACUU

UCCACUGAAA CCUGGU

SEQ ID NO: 2:
KB208E9 cDNA -
ACCAGGTTTCAGTGGAAAGTATTGCCTCAGGGATGCTTAATAGTTCAACTATTTGTC

AGCTCAAGCTCTGCAACCAGTTAGAGACAAGITTTCAGACTGITACATCGTTCACTAT

GTTGATATTTTGTOTGCTGCAGAAACGAGAGACAATTAATTGACCGTTACACATTTC

TGCAGACAGAGGTTGCCAACGCGGGACTGACAATAACATCTGATAAGATTCAAACC

TCTACTCCTTTCCGTTACTTGOGAATGCAGGTAGAGGAAAGGAAAATTAAACCAC

SEQ ID NO: 3:
Forward primer -
5'-TGCCTCAGGGAATGCTTAAT

SEQ ID NO: 4:
Reverse Primer -
5'-CCTCTACCTGCATTCCCAAG

SEQ ID NO: 5:
rp11-442e11 cDNA -
TTACCAGGTT GAAATGGGAA ACGAGGGAGA AAGGACTTGA AGATGACTCC

AGTGTTTCTA GTAACACAGG TGGTGATGTC ACTAATGAGG GTAAAAGCAC

TGAAAGCGCA GGTATGACTT TGGAAAATGG TGGGTTTGAG GTGTTTCTTC

CCAAGCAAGT ATTGGGGATT CATGCCAAGA ACTTAAGAGT GGTACCAGGG

CCAGACATAT AAATTTGGGG TATTTATATC AAATGCTGGT AGAAGTAGCG

AGATTAAAAG AGTTAGCCCT GAGAAAACAT AGAGCAAGGA GAGGCAGTTA

AAATCAGCAG AGCCTGCTGA AAAACACCTT CTGTAGAAGG TAG

SEQ ID NO: 6:
rp11-442e11 cDNA -
CTACCTTCTACAGAAGGIGITTITCAGCAGGCTCTGCTGATITTAACTGCCTCTCCTIGC

TCTATGTTTTCTCAGGGCTAACTCTTTTAATCTCGCTACTICTACCAGCATTTGATATA

AATACCCCAAATTTATATGTCTGGCCCTGGTACCACTCTTAAGTTCTTGGCATGAATC

CCCAATACTTGCTTGGGAAGAAACACCTCAAACCCACCATTTTCCAAAGTCATACCT

GCGCTTTCAGTGCTTTTACCCICATTAGTGACATCACCACCTGIGTTACTAGAAACACT

GGAGTCA TCTTCAAGTCCTTTCTCCCTCGTTTCCCATTTCAACCTGGTAA

SEQ ID NO: 7:
Forward primer -
5'-GGTGTTTTTCAGCAGGCTCT
```

SEQUENCE LISTING

SEQ ID NO: 8:
Reverse primer -
5'-AAAATGGTGGGTTTGAGGTG

SEQ ID NO: 9:
Forward primer -
5'-GATTTTCACCAATGACCGCCG

SEQ ID NO: 10:
Reverse primer -
5'-CCCCAGCATTGATGTCG

SEQ ID NO: 11:
Forward primer -
5'-CAGGGGAAACAGACGATGACAACT

SEQ ID NO: 12:
Reverse primer -
5'-TGCGGTAACCCAAGCCACACT

SEQ ID NO: 13:
Forward primer -
5'-GAGCCAAAAGTTCTTCTACACTGC

SEQ ID NO: 14:
Reverse primer -
5'-AGATTCCAGATGGTTCTGCCTA

SEQ ID NO: 15:
Forward primer -
5'-GAGATCCCTCCAAAATCAAGTG

SEQ ID NO: 16:
Reverse primer -
5'-CCTTCCACGATACCAAAGTTGT

REFERENCES

1. Mazzucchelli, R., Colanzi, P., Pornante, R., Muzzonigro, G. & Montironi, R. (2000) *Adv Clin Path* 4, 111-20.
2. Schamhart, D. H., Maiazza, R. & Kurth. K. H. (2005) *Int Oncol* 26, 565-77.
3. Thompson, 1. M., Pauler, D. K., Goodman, P. J., Tangen, C. M., Lucia, M. S., Parnes, H. L., Minasian, L. M., Ford, L. G., Lippman, S. M., Crawford, E. D., Crowley, J. J. & Coltman, C. A. Jr. (2004) *N Engl Med* 350, 2239-46.
4. Martin, K. J., Graner, E., Li, Y., Price, L. M., Kritzman, B. M., Fournier, M. V., Rhei, E. & Pardee, A. B. (2001) *Proc Mal Acad Sci USA* 98, 2646-51.
5. Liang, P. & Pardee, A. B. (1998) *Mol Biotechnol* 10, 261-7.
6. Kim, M. Y., Park, E., Park, J. H., Park, D. H., Moon. W. S., Cho, B. H., Shin, R S. & Kim, D. G. (2001) *Oncogene* 20, 4568-75.
7. Chakrabarti, R., Robles, L. D., Gibson, J. & Muroski, M. (2002) *Cancer Genet Cytogenet* 139, 115-25.
8. Liang, P. & Pardee, A. B. (2003) *Nat Rev Cancer* 3, 869-76.
9. Patel, K., Whelan, P. J., Prescott, S., Brownhill, S. C., Johnston, C. F., Selby, P. J. & Burchill, S. A. (2004) *Clin Cancer Res* 10, 7511-9.
10. Zhang, L. & Barritt, G. J. (2004) *Cancer Res* 64, 8365-73.
11. Tsavaler, L., Shapero, M. H., Morkowski, S. & Laus, R. (2001) *Cancer Res* 61, 3760-9.
12. Sakko, A. J., Ricciardelli, C., Mayne, K., Suwiwat, S., LeBaron, R. G., Marshall, V. R., Tilley. W. D. & Horsfall, D. J. (2003) *Cancer Res* 63, 4786-91.
13. Cross, N. A., Chandrasekharan, S., Jokonya, N., Fowles, A., Hamdy, F. C., Buttle, D. J. & Eaton, C. L. (2005) *Prostate* 63, 269-75.
14. Boller, K., Konia, H., Sauter, M., Mueller-Lantzsch, N., Lower, R., Lower, J. & Kurth, R. (1993) *Virology* 196, 349-53.
15. Ejthadi, H. D., Martin, J. H., Junying, J., Roden, D. A., Lahiri, M., Warren, P., Murray. P. G. & Nelson. P. N. (2005) *Arch Viral* 150, 177-84.
16. Goessl, C. Krause, H., Muller, M., Heicappell, R., Schrader, M., Sachsinger, J. & Miller, K. (2000) *Cancer Res* 60, 5941-5.
17. Paul, B., Dhir, R., Landsittel, D., Hitchens, M. R. & Getzenberg, R. H. (2005) *Cancer Res* 65, 4097-100.
18. Tombal, B., Van Cangh, P. J., Lark, S. & Gala, J. L. (2003) *Prostate* 56, 163-70.
19. Zimmerman, R. A. & Culkin, D. J. (2003) *Clin Prostate Cancer* 2, 160-6.
20. Wang, Z. P., Eisenbemer, M. A., Carducci, M. A., Partin, A. W., Scher, H. I. & Ts'o, P. 0. (2000) *Cancer* 88, 2787-95.
21. Ts'o, P. O., Pannek, J., Wang, Z. P., Lesko, S. A., Bova, G. S. & Partin, A. W. (1997) *Urology* 49, 881-5.
22. Fehm, T., Sagalowsky, A., Clifford, E., Beitsch, P., Saboorian, H., Euhus, D., Meng. S., Morrison, L., Tucker, T., Lane, N., Ghadimi, B. M., Heselmeyer-Haddad, K., Ried, T., Rao. C. & Uhr, J. (2002) *Clin Cancer Res* 8, 2073-84.
23. Liotta, l-A. & Kohn, E. C. (2003) *Nat Genet* 33, 10-1.
24. Ramaswamy, S., Ross, K. N., Lander, E. S. & Golub, T. R. (2003) *Nat Genet* 33, 49-54.

25. Chattedee, S. K. & Zetter, B. R. (2005) *Future Oncol* 1, 37-50.
26. Tricoli, J. V., Schoenfeldt, M. & Conley, B. A. (2004) *Clin Cancer Res* 10, 3943-53.
27. Hutchinson, L. M., Chang, E. L., Becker, C. M., Ushiyama, N., Behonick, D., Shih, M. C., DeWolf, W. C., Gaston, S. M. & Zetter. B. R. (2005) *Clin Biochem* 38, 558-71.
28. Jenial, A., Murray, T. Ward. E. Samuels, A., Tiwari, R. C., Ghafoor, A., Feuer, E. & Thun, M. J. (2005) *CA Cancer Clin* 55, 10-30.
29. Scher, H. 1. & Heller. G. (2000) *Urology* 55, 323-7.
30. Magee, J. A. Araki, T., Patil, S., Ebrig, T., True, L., Humphrey, P. A., Catalona, W. J., Watson, M. A. & Milbrandt, J. (2001) *Cancer Res* 61, 5692-6.
31. Jeronimo, C., Usadel, Henrique, R., Oliveira, J., Lopes, C., Nelson, W. G. & Sidransky, D. (2001), *I Nall Cancer Inst* 93, 1747-52.
32. Dhanasekaran, S. M., Barrette, T. R., Ghosh, D., Shah, R., Varambally, S., Kurachi, K., Pienta, K. J., Rubin, M. A. & Chinnaiyan, A. M. (2001) *Nature* 412, 822-6.
33. Chaib, H., Cockrell, E. K., Rubin, M. A. & Macoska, J. A. (2001) *Neoplasia* 3, 43-52.
34. Bubendorf, L. Kolmer, M., Kononen, J. Koivisto, P., Mousses, S., Chen, Y., Mahlamaki, E., Schraml, P., Moch, H., Willi, N., Elkahloun, A. G. Pretlow, T. G., Gasser, T. C., Mihatsch, M. J., Sauter, G. & Kallioniemi, 0. P. (1999) *J Nall Cancer Inst* 91, 1758-64.
35. Singh, D. Febbo, P. G., Ross, K., Jackson, D. G., Manola, J., Ladd, C., Tamayo, P., Renshaw, A. A., D'Amico, A. V. Richie, J. P., Lander, E. S. Loda, M., Kantoff, P. W. Golub, T. R. & Sellers, W. R. (2002) *Cancer Cell* 1, 203-9.
36. Lapointe, J., Li, C., Higgins, J. P., van de Rijn, M., Bair, E., Montgomery, K., Ferrari, M., Egevad, L., Rayford, W., BerQerheim, U., Ek.man, P., DeMarzo, A. M., Tibshirani, R., Botstein, D., Brown, P. 0., Brooks, J. D. & Pollack, J. R. (2004) *Proc Nntl Acad Sci USA* 101, 811-6.
37. True, L., Coleman, I, Hawley, S., Huang, C. Y., Gifford, D., Coleman, R., Beer, T. M., Gelmann, E., Datta, M., Mostaghel, E., Knudsen, B., Lange, P., Vessella, R., Lin, D., Hood. L. & Nelson, P. S. (2006) *Proc Nall Acad Sci USA* 103, 10991-6.
38. Weinberg, R. A. (2007) in *The biology of cancer* (Garland Science, New York), pp. 587-654.
39. Menke, T. B. & Warnecke, J. M. (2004) *Ann NY Acad Sci* 1022, 185-9.
40. Altschul, S. F., Madden, T. L., Schaffer, A. A., Mang, J., Zhang, Z., Miller, W. & Lipman, D. J. (1997) *Nucleic Acids Res* 25, 3389-402.

What is claimed:

1. A method for treating prostate cancer in a human subject, the method comprising:
   a. providing a sample of prostate tissue, blood, or urine from the subject;
   b. determining the level of expression of SEQ ID NO: 1 and the expression of SEQ ID NO: 5 in the sample, wherein if a ratio of expression of SEQ ID NO: 1 and the expression of SEQ ID NO: 5 in the sample is greater than 3, the subject is diagnosed as having prostate cancer; and
   c. administering a therapeutically effective prostate cancer treatment selected from the group consisting of an androgen receptor (AR)-targeted therapy, an antimicrotubule agent, an alkylating agent and an anthracenedione to the subject diagnosed with prostate cancer to treat the prostate cancer.

2. The method according to claim 1, wherein the determining step comprises determining the expression of SEQ ID NO: 5 by a reverse transcriptase polymerase chain reaction assay.

3. The method according to claim 1, wherein the subject's sample is a blood or a urine sample.

4. The method according to claim 3, wherein the subject's sample is a blood, plasma, serum, or urine sample.

5. The method according to claim 1 wherein determining the level of expression of SEQ ID NO: 1 and the level of expression of SEQ ID NO: 5 in the sample comprises the provision and use of SEQ ID NO: 3 as a forward primer and/or SEQ ID NO: 4 as a reverse primer in the reverse transcriptase polymerase chain reaction assay to determine the level of expression of SEQ ID NO: 1, and the provision and use of SEQ ID NO: 7as a forward primer and/or SEQ ID NO: 8 as a reverse primer in the reverse transcriptase polymerase chain reaction assay to determine the level of expression of SEQ ID NO: 5.

6. The method according to claim 1 wherein if a ratio, comprising a quotient calculated by determining the level of expression of SEQ ID NO: 1 divided by the level of expression of SEQ ID NO: 5, is greater than 1.5, then the subject is administered a cancer treatment selected from the group consisting of an anti-androgen, an antimicrotubule agent, an alkylating agent and an anthracenedione to the subject to treat the prostate cancer.

7. A method for treating localized or advanced prostate cancer in a human subject not previously treated with hormonal therapy, chemotherapy or radiation therapy, the method comprising:
   a. providing a sample of prostate tissue, blood, or urine from the subject;
   b. determining the level of expression of SEQ ID NO: 1 and the level of expression of SEQ ID NO: 5 in the sample, wherein if a ratio of expression of SEQ ID NO: 1 and the expression of SEQ ID NO: 5 in the sample is greater than 3, then the subject is diagnosed as having localized or advanced prostate cancer; and
   c. administering an androgen receptor (AR)-targeted therapy cancer treatment to the subject diagnosed with localized or advanced prostate cancer to treat the localized or advanced prostate cancer in the human subject.

8. The method according to claim 7, wherein the an androgen receptor (AR)-targeted therapy cancer treatment can include one or more drugs that bind to: a) the ligand binding domain of AR; b) drugs that bind to the N-terminal transactivation domain of AR; c) drugs that inhibit co-regulators of androgen receptor; and d) drugs that suppress dihydrotestosterone (DHT) synthesis.

9. The method according to claim 8, wherein the drugs that bind to the ligand binding domain of AR, include enzalutamide, ARN-509, or ODM-201.

10. The method according to claim 8, wherein the drugs that bind to the N-terminal transactivation domain of AR, include EPI-001.

11. The method according to claim 8, wherein the drugs that inhibit co-regulators of androgen receptor, including hydrazinobenzoylcurcumin (HBC).

12. The method according to claim 8, wherein the drugs that suppress dihydrotestosterone (DHT) synthesis, include aberaterone, geleterone, or seviteronel.

13. The method according to claim 7, wherein the determining steps comprise determining the level of SEQ ID NO: 1 and SEQ ID NO: 5 by a reverse transcriptase polymerase chain reaction assay.

14. The method according to claim 7, wherein the subject's sample is a blood or a urine sample.

15. The method according to claim 14, wherein the subject's sample is a blood, serum, plasma, or urine sample.

16. The method according to claim 7 wherein determining the level of expression of SEQ ID NO: 1 and the level of expression of SEQ ID NO: 5 in the sample comprises the provision and use of SEQ ID NO: 3 as a forward primer and/or SEQ ID NO: 4 as a reverse primer in the reverse transcriptase polymerase chain reaction assay to determine the level of expression of SEQ ID NO: 1, and the provision and use of SEQ ID NO: 7 as a forward primer and/or SEQ ID NO: 8 as a reverse primer in the reverse transcriptase polymerase chain reaction assay to determine the level of expression of SEQ ID NO: 5.

* * * * *